United States Patent
Castella et al.

(10) Patent No.: US 10,219,780 B2
(45) Date of Patent: Mar. 5, 2019

(54) OCT-IVUS CATHETER FOR CONCURRENT LUMINAL IMAGING

(75) Inventors: Paul Castella, San Antonio, TX (US); Nathaniel J. Kemp, Austin, TX (US); Thomas E. Milner, Austin, TX (US); David G. Rosenbaum, Glencoe, IL (US)

(73) Assignee: Volcano Corporation, San Diego, CA (US)

( * ) Notice: Subject to any disclaimer, the term of this patent is extended or adjusted under 35 U.S.C. 154(b) by 814 days.

(21) Appl. No.: 12/173,004

(22) Filed: Jul. 14, 2008

(65) Prior Publication Data

US 2009/0043191 A1    Feb. 12, 2009

Related U.S. Application Data

(60) Provisional application No. 60/949,472, filed on Jul. 12, 2007, provisional application No. 60/949,511, filed on Jul. 12, 2007.

(51) Int. Cl.
    *A61B 8/12*     (2006.01)
    *A61B 5/00*     (2006.01)
    *A61B 5/02*     (2006.01)
    *A61B 8/08*     (2006.01)

(52) U.S. Cl.
    CPC .............. *A61B 8/12* (2013.01); *A61B 5/0066* (2013.01); *A61B 5/02007* (2013.01); *A61B 5/6852* (2013.01); *A61B 8/486* (2013.01)

(58) Field of Classification Search
    CPC . A61B 5/0066; A61B 5/02007; A61B 5/6852; A61B 8/12; A61B 8/486
    USPC ......... 600/112, 407, 411, 427, 47, 462, 466, 600/467
    See application file for complete search history.

(56) References Cited

U.S. PATENT DOCUMENTS

| | | |
|---|---|---|
| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |

(Continued)

FOREIGN PATENT DOCUMENTS

| | | |
|---|---|---|
| EP | 1041373 A2 | 10/2000 |
| EP | 01172637 A1 | 1/2002 |

(Continued)

OTHER PUBLICATIONS

Fiber Optics, "The Basics of Fiber Optic Cable: A Tutorial", accessed online Nov. 26, 2014, available online as early as Feb. 2001.*

(Continued)

*Primary Examiner* — Christopher L Cook

(57) ABSTRACT

The invention relates to an apparatus for in vivo imaging. More specifically, the present invention relates to a catheter that incorporates an Optical Coherence Tomography (OCT) system and an Intravascular Ultrasound ("IVUS) system for concurrent imaging of luminal systems, such as imaging the vasculature system, including, without limitation, cardiac vasculature, peripheral vasculature and neural vasculature.

16 Claims, 4 Drawing Sheets

(56) References Cited

U.S. PATENT DOCUMENTS

| | | | |
|---|---|---|---|
| 4,432,370 A | 2/1984 | Hughes et al. | |
| 4,552,554 A | 11/1985 | Gould et al. | |
| 4,577,543 A | 3/1986 | Wilson | 87/11 |
| 4,676,980 A | 6/1987 | Segal et al. | |
| 4,682,895 A | 7/1987 | Costello | |
| 4,733,665 A | 3/1988 | Palmaz | |
| 4,744,619 A | 5/1988 | Cameron | |
| 4,762,129 A | 8/1988 | Bonzel | |
| 4,766,386 A | 8/1988 | Oliver et al. | |
| 4,771,774 A | 9/1988 | Simpson et al. | |
| 4,794,931 A | 1/1989 | Yock | |
| 4,800,886 A * | 1/1989 | Nestor | 600/311 |
| 4,803,639 A | 2/1989 | Steele et al. | |
| 4,816,567 A | 3/1989 | Cabilly et al. | |
| 4,819,740 A | 4/1989 | Warrington | |
| 4,821,731 A | 4/1989 | Martinelli et al. | |
| 4,824,435 A | 4/1989 | Giesy et al. | |
| 4,830,023 A | 5/1989 | de Toledo et al. | |
| 4,834,093 A | 5/1989 | Littleford et al. | |
| 4,841,977 A | 6/1989 | Griffith et al. | |
| 4,864,578 A | 9/1989 | Proffitt et al. | |
| 4,873,690 A | 10/1989 | Adams | |
| 4,877,314 A | 10/1989 | Kanamori | |
| 4,887,606 A | 12/1989 | Yock et al. | |
| 4,917,085 A | 4/1990 | Smith | |
| 4,917,097 A | 4/1990 | Proudian et al. | |
| 4,928,693 A | 5/1990 | Goodin et al. | |
| 4,932,413 A | 6/1990 | Shockey et al. | |
| 4,932,419 A | 6/1990 | de Toledo | |
| 4,948,229 A | 8/1990 | Soref | |
| 4,951,677 A | 8/1990 | Crowley et al. | |
| 4,969,742 A | 11/1990 | Falk et al. | |
| 4,987,412 A | 1/1991 | Vaitekunas et al. | |
| 4,993,412 A | 2/1991 | Murphy-Chutorian | |
| 4,998,972 A | 3/1991 | Chin et al. | |
| 5,000,185 A | 3/1991 | Yock | |
| 5,024,234 A | 6/1991 | Leary et al. | 128/663.01 |
| 5,025,445 A | 6/1991 | Anderson et al. | |
| 5,032,123 A | 7/1991 | Katz et al. | |
| 5,037,169 A | 8/1991 | Chun | |
| 5,039,193 A | 8/1991 | Snow et al. | |
| 5,040,548 A | 8/1991 | Yock | |
| 5,041,108 A | 8/1991 | Fox et al. | |
| 5,054,492 A | 10/1991 | Scribner et al. | |
| 5,065,010 A | 11/1991 | Knute | |
| 5,065,769 A | 11/1991 | de Toledo | |
| 5,085,221 A * | 2/1992 | Ingebrigtsen et al. | 600/446 |
| 5,095,911 A | 3/1992 | Pomeranz | |
| 5,100,424 A | 3/1992 | Jang et al. | |
| 5,120,308 A | 6/1992 | Hess | |
| 5,125,137 A | 6/1992 | Corl et al. | |
| 5,135,486 A | 8/1992 | Eberle et al. | |
| 5,135,516 A | 8/1992 | Sahatjian et al. | |
| 5,155,439 A | 10/1992 | Holmbo et al. | |
| 5,158,548 A | 10/1992 | Lau et al. | |
| 5,163,445 A | 11/1992 | Christian et al. | |
| 5,167,233 A | 12/1992 | Eberle et al. | |
| 5,174,295 A | 12/1992 | Christian et al. | |
| 5,176,141 A | 1/1993 | Bom et al. | |
| 5,176,674 A | 1/1993 | Hofmann | |
| 5,178,159 A | 1/1993 | Christian | |
| 5,183,048 A | 2/1993 | Eberle | |
| 5,188,632 A | 2/1993 | Goldenberg | |
| 5,201,316 A | 4/1993 | Pomeranz et al. | |
| 5,202,745 A | 4/1993 | Sorin et al. | |
| 5,203,779 A | 4/1993 | Muller et al. | |
| 5,220,922 A | 6/1993 | Barany | |
| 5,224,953 A | 7/1993 | Morgentaler | |
| 5,226,421 A | 7/1993 | Frisbie et al. | |
| 5,240,003 A | 8/1993 | Lancee et al. | |
| 5,240,437 A | 8/1993 | Christian | |
| 5,242,460 A | 9/1993 | Klein et al. | |
| 5,243,988 A | 9/1993 | Sieben et al. | |
| 5,257,974 A | 11/1993 | Cox | |
| 5,266,302 A | 11/1993 | Peyman et al. | |

| | | | |
|---|---|---|---|
| 5,267,954 A | 12/1993 | Nita | |
| 5,301,001 A | 4/1994 | Murphy et al. | |
| 5,312,425 A | 5/1994 | Evans et al. | |
| 5,313,949 A | 5/1994 | Yock | |
| 5,313,957 A | 5/1994 | Little | |
| 5,319,492 A | 6/1994 | Dorn et al. | |
| 5,321,501 A | 6/1994 | Swanson et al. | |
| 5,325,198 A | 6/1994 | Hartley et al. | |
| 5,336,178 A | 8/1994 | Kaplan et al. | |
| 5,346,689 A | 9/1994 | Peyman et al. | |
| 5,348,017 A | 9/1994 | Thornton et al. | |
| 5,348,481 A | 9/1994 | Ortiz | |
| 5,353,798 A | 10/1994 | Sieben | |
| 5,358,409 A | 10/1994 | Obara | |
| 5,358,478 A | 10/1994 | Thompson et al. | |
| 5,368,037 A | 11/1994 | Eberle et al. | |
| 5,373,845 A | 12/1994 | Gardineer et al. | |
| 5,373,849 A | 12/1994 | Maroney et al. | |
| 5,375,602 A | 12/1994 | Lancee et al. | |
| 5,377,682 A | 1/1995 | Ueno et al. | |
| 5,383,853 A | 1/1995 | Jung et al. | 604/96 |
| 5,387,193 A | 2/1995 | Miraki | |
| 5,396,328 A | 3/1995 | Jestel et al. | |
| 5,397,355 A | 3/1995 | Marin et al. | |
| 5,405,377 A | 4/1995 | Cragg | |
| 5,411,016 A | 5/1995 | Kume et al. | |
| 5,419,777 A | 5/1995 | Hofling | |
| 5,421,338 A | 6/1995 | Crowley et al. | |
| 5,423,806 A | 6/1995 | Dale et al. | |
| 5,427,118 A | 6/1995 | Nita et al. | |
| 5,431,673 A | 7/1995 | Summers et al. | |
| 5,436,759 A | 7/1995 | Dijaili et al. | |
| 5,439,139 A | 8/1995 | Brovelli | |
| 5,443,457 A | 8/1995 | Ginn et al. | 604/280 |
| 5,453,575 A | 9/1995 | O'Donnell et al. | |
| 5,456,693 A | 10/1995 | Conston et al. | |
| 5,459,570 A | 10/1995 | Swanson et al. | |
| 5,480,388 A | 1/1996 | Zadini et al. | |
| 5,485,845 A | 1/1996 | Verdonk et al. | |
| 5,492,125 A | 2/1996 | Kim et al. | |
| 5,496,997 A | 3/1996 | Pope | |
| 5,507,761 A | 4/1996 | Duer | |
| 5,512,044 A | 4/1996 | Duer | |
| 5,514,128 A | 5/1996 | Hillsman et al. | |
| 5,529,674 A | 6/1996 | Hedgcoth | 204/298.21 |
| 5,541,730 A | 7/1996 | Chaney | |
| 5,546,717 A | 8/1996 | Penczak et al. | |
| 5,546,948 A | 8/1996 | Hamm et al. | |
| 5,565,332 A | 10/1996 | Hoogenboom et al. | |
| 5,573,520 A | 11/1996 | Schwartz et al. | |
| 5,581,638 A | 12/1996 | Givens et al. | |
| 5,586,054 A | 12/1996 | Jensen et al. | |
| 5,592,939 A | 1/1997 | Martinelli | |
| 5,596,079 A | 1/1997 | Smith et al. | |
| 5,598,844 A | 2/1997 | Diaz et al. | |
| 5,609,606 A | 3/1997 | O'Boyle | |
| 5,630,806 A | 5/1997 | Inagaki et al. | |
| 5,651,366 A | 7/1997 | Liang et al. | |
| 5,660,180 A | 8/1997 | Malinowski et al. | |
| 5,667,499 A | 9/1997 | Welch et al. | 604/282 |
| 5,667,521 A | 9/1997 | Keown | 606/194 |
| 5,672,877 A | 9/1997 | Liebig et al. | |
| 5,674,232 A | 10/1997 | Halliburton | |
| 5,693,015 A | 12/1997 | Walker et al. | |
| 5,713,848 A | 2/1998 | Dubrul et al. | |
| 5,745,634 A | 4/1998 | Garrett et al. | |
| 5,771,895 A | 6/1998 | Slager | |
| 5,779,731 A | 7/1998 | Leavitt | |
| 5,780,958 A | 7/1998 | Strugach et al. | |
| 5,798,521 A | 8/1998 | Froggatt | |
| 5,800,450 A | 9/1998 | Lary et al. | |
| 5,803,083 A | 9/1998 | Buck et al. | |
| 5,814,061 A | 9/1998 | Osborne et al. | |
| 5,817,025 A | 10/1998 | Alekseev et al. | |
| 5,820,594 A | 10/1998 | Fontirroche et al. | |
| 5,824,520 A | 10/1998 | Mulligan-Kehoe | |
| 5,827,313 A | 10/1998 | Ream | |
| 5,830,222 A | 11/1998 | Makower | |
| 5,848,121 A | 12/1998 | Gupta et al. | |

(56) References Cited

U.S. PATENT DOCUMENTS

| | | | |
|---|---|---|---|
| 5,851,464 A | 12/1998 | Davila et al. | 264/103 |
| 5,857,974 A | 1/1999 | Eberle et al. | |
| 5,872,829 A | 2/1999 | Wischmann et al. | |
| 5,873,835 A | 2/1999 | Hastings et al. | |
| 5,882,722 A | 3/1999 | Kydd | |
| 5,912,764 A | 6/1999 | Togino | |
| 5,916,194 A | 6/1999 | Jacobsen et al. | |
| 5,921,931 A | 7/1999 | O'Donnell et al. | |
| 5,925,055 A | 7/1999 | Adrian et al. | |
| 5,949,929 A | 9/1999 | Hamm | |
| 5,951,586 A | 9/1999 | Berg et al. | |
| 5,974,521 A | 10/1999 | Akerib | |
| 5,976,120 A | 11/1999 | Chow et al. | 604/525 |
| 5,978,391 A | 11/1999 | Das et al. | |
| 5,997,523 A | 12/1999 | Jang | |
| 6,021,240 A | 2/2000 | Murphy et al. | |
| 6,022,319 A | 2/2000 | Willard et al. | |
| 6,031,071 A | 2/2000 | Mandeville et al. | |
| 6,036,889 A | 3/2000 | Kydd | |
| 6,043,883 A | 3/2000 | Leckel et al. | |
| 6,050,949 A | 4/2000 | White et al. | 600/466 |
| 6,059,738 A | 5/2000 | Stoltze et al. | |
| 6,068,638 A | 5/2000 | Makower | |
| 6,074,362 A | 6/2000 | Jang et al. | |
| 6,078,831 A | 6/2000 | Belef et al. | |
| 6,080,109 A | 6/2000 | Baker et al. | |
| 6,091,496 A | 7/2000 | Hill | |
| 6,094,591 A | 7/2000 | Foltz et al. | |
| 6,095,976 A | 8/2000 | Nachtomy et al. | |
| 6,097,755 A | 8/2000 | Guenther, Jr. et al. | |
| 6,099,471 A | 8/2000 | Torp et al. | |
| 6,099,549 A | 8/2000 | Bosma et al. | |
| 6,102,938 A | 8/2000 | Evans et al. | |
| 6,106,476 A | 8/2000 | Corl et al. | |
| 6,120,445 A | 9/2000 | Grunwald | |
| 6,123,673 A | 9/2000 | Eberle et al. | |
| 6,134,003 A | 10/2000 | Tearney et al. | |
| 6,139,510 A | 10/2000 | Palermo | |
| 6,141,089 A | 10/2000 | Thoma et al. | |
| 6,146,328 A | 11/2000 | Chiao et al. | |
| 6,148,095 A | 11/2000 | Prause et al. | |
| 6,151,433 A | 11/2000 | Dower et al. | |
| 6,152,877 A | 11/2000 | Masters | |
| 6,152,878 A | 11/2000 | Nachtomy et al. | |
| 6,159,225 A | 12/2000 | Makower | |
| 6,165,127 A | 12/2000 | Crowley | |
| 6,176,842 B1 | 1/2001 | Tachibana et al. | |
| 6,179,809 B1 | 1/2001 | Khairkhahan et al. | |
| 6,186,949 B1 | 2/2001 | Hatfield et al. | |
| 6,190,353 B1 | 2/2001 | Makower et al. | |
| 6,200,266 B1 | 3/2001 | Shokrollahi et al. | |
| 6,200,268 B1 | 3/2001 | Vince et al. | |
| 6,203,537 B1 | 3/2001 | Adrian | |
| 6,208,415 B1 | 3/2001 | De Boer et al. | |
| 6,210,332 B1 | 4/2001 | Chiao et al. | |
| 6,210,339 B1 | 4/2001 | Kiepen et al. | |
| 6,212,308 B1 | 4/2001 | Donald | |
| 6,231,518 B1 | 5/2001 | Grabek et al. | |
| 6,245,066 B1 | 6/2001 | Morgan et al. | |
| 6,249,076 B1 | 6/2001 | Madden et al. | |
| 6,254,543 B1 | 7/2001 | Grunwald et al. | |
| 6,256,090 B1 | 7/2001 | Chen et al. | |
| 6,258,052 B1 | 7/2001 | Milo | |
| 6,261,246 B1 | 7/2001 | Pantages et al. | |
| 6,275,628 B1 | 8/2001 | Jones et al. | |
| 6,283,921 B1 | 9/2001 | Nix et al. | |
| 6,283,951 B1 | 9/2001 | Flaherty et al. | |
| 6,295,308 B1 | 9/2001 | Zah | |
| 6,299,622 B1 | 10/2001 | Snow et al. | |
| 6,312,384 B1 | 11/2001 | Chiao | |
| 6,325,797 B1 | 12/2001 | Stewart et al. | |
| 6,328,696 B1 | 12/2001 | Fraser | |
| 6,343,168 B1 | 1/2002 | Murphy et al. | |
| 6,343,178 B1 | 1/2002 | Burns et al. | |
| 6,350,240 B1 | 2/2002 | Song et al. | |
| 6,364,841 B1 | 4/2002 | White et al. | 600/466 |
| 6,366,722 B1 | 4/2002 | Murphy et al. | |
| 6,367,984 B1 | 4/2002 | Stephenson et al. | |
| 6,373,970 B1 | 4/2002 | Dong et al. | |
| 6,375,615 B1 | 4/2002 | Flaherty et al. | |
| 6,375,618 B1 | 4/2002 | Chiao et al. | |
| 6,375,628 B1 | 4/2002 | Zadno-Azizi et al. | |
| 6,376,830 B1 | 4/2002 | Froggatt et al. | |
| 6,379,352 B1 | 4/2002 | Reynolds et al. | |
| 6,381,350 B1 | 4/2002 | Klingensmith et al. | |
| 6,387,124 B1 | 5/2002 | Buscemi et al. | |
| 6,396,976 B1 | 5/2002 | Little et al. | |
| 6,398,792 B1 | 6/2002 | O'Connor | |
| 6,417,948 B1 | 7/2002 | Chowdhury et al. | |
| 6,419,644 B1 | 7/2002 | White et al. | 600/585 |
| 6,421,164 B2 | 7/2002 | Tearney et al. | |
| 6,423,012 B1 | 7/2002 | Kato et al. | |
| 6,426,796 B1 | 7/2002 | Pulliam et al. | |
| 6,428,041 B1 | 8/2002 | Wohllebe et al. | |
| 6,428,498 B2 | 8/2002 | Uflacker | |
| 6,429,421 B1 | 8/2002 | Meller et al. | |
| 6,440,077 B1 | 8/2002 | Jung et al. | |
| 6,443,903 B1 | 9/2002 | White et al. | 600/466 |
| 6,450,964 B1 | 9/2002 | Webler | |
| 6,457,365 B1 | 10/2002 | Stephens et al. | |
| 6,459,844 B1 | 10/2002 | Pan | |
| 6,468,290 B1 | 10/2002 | Weldon et al. | |
| 6,475,149 B1 | 11/2002 | Sumanaweera | |
| 6,480,285 B1 | 11/2002 | Hill | |
| 6,491,631 B2 | 12/2002 | Chiao et al. | |
| 6,491,636 B2 | 12/2002 | Chenal et al. | |
| 6,501,551 B1 | 12/2002 | Tearney et al. | |
| 6,504,286 B1 | 1/2003 | Porat et al. | |
| 6,508,824 B1 | 1/2003 | Flaherty et al. | |
| 6,514,237 B1 | 2/2003 | Maseda | |
| 6,520,269 B2 | 2/2003 | Geiger et al. | |
| 6,520,677 B2 | 2/2003 | Iizuka | |
| 6,535,764 B2 | 3/2003 | Imran et al. | |
| 6,538,778 B1 | 3/2003 | Leckel et al. | |
| 6,544,217 B1 | 4/2003 | Gulachenski | |
| 6,544,230 B1 | 4/2003 | Flaherty et al. | |
| 6,545,760 B1 | 4/2003 | Froggatt et al. | |
| 6,546,272 B1 | 4/2003 | MacKinnon et al. | |
| 6,551,250 B2 | 4/2003 | Khalil | |
| 6,566,648 B1 | 5/2003 | Froggatt | |
| 6,570,894 B2 | 5/2003 | Anderson | |
| 6,572,555 B2 | 6/2003 | White et al. | 600/166 |
| 6,579,311 B1 | 6/2003 | Makower | |
| 6,584,335 B1 | 6/2003 | Haar et al. | |
| 6,592,612 B1 | 7/2003 | Samson et al. | |
| 6,594,448 B2 | 7/2003 | Herman et al. | |
| 6,602,241 B2 | 8/2003 | Makower et al. | |
| 6,611,322 B1 | 8/2003 | Nakayama et al. | |
| 6,611,720 B2 | 8/2003 | Hata et al. | |
| 6,612,992 B1 | 9/2003 | Hossack et al. | |
| 6,615,062 B2 | 9/2003 | Ryan et al. | |
| 6,615,072 B1 | 9/2003 | Izatt et al. | |
| 6,621,562 B2 | 9/2003 | Durston | |
| 6,631,284 B2 | 10/2003 | Nutt et al. | |
| 6,638,227 B2 | 10/2003 | Bae | |
| 6,645,152 B1 | 11/2003 | Jung et al. | |
| 6,646,745 B2 | 11/2003 | Verma et al. | |
| 6,655,386 B1 | 12/2003 | Makower et al. | |
| 6,659,957 B1 | 12/2003 | Vardi et al. | |
| 6,660,024 B1 | 12/2003 | Flaherty et al. | |
| 6,663,565 B2 | 12/2003 | Kawagishi et al. | |
| 6,665,456 B2 | 12/2003 | Dave et al. | |
| 6,669,716 B1 | 12/2003 | Gilson et al. | 623/1.11 |
| 6,671,055 B1 | 12/2003 | Wavering et al. | |
| 6,673,015 B1 | 1/2004 | Glover et al. | |
| 6,673,064 B1 | 1/2004 | Rentrop | |
| 6,685,648 B1 | 2/2004 | Flaherty et al. | |
| 6,689,056 B1 | 2/2004 | Kilcoyne et al. | |
| 6,689,144 B2 | 2/2004 | Gerberding | 606/157 |
| 6,696,173 B1 | 2/2004 | Naundorf et al. | |
| 6,701,044 B2 | 3/2004 | Arbore et al. | |
| 6,701,176 B1 | 3/2004 | Halperin et al. | |
| 6,709,444 B1 | 3/2004 | Makower | |
| 6,712,836 B1 | 3/2004 | Berg et al. | |

(56) References Cited

U.S. PATENT DOCUMENTS

| | | | |
|---|---|---|---|
| 6,714,703 B2 | 3/2004 | Lee et al. | |
| 6,719,717 B1 | 4/2004 | Johnson et al. | |
| 6,725,073 B1 | 4/2004 | Motamedi et al. | |
| 6,726,677 B1 | 4/2004 | Flaherty et al. | |
| 6,730,107 B2 | 5/2004 | Kelley et al. | |
| 6,733,474 B2 | 5/2004 | Kusleika | |
| 6,738,144 B1 | 5/2004 | Dogariu | |
| 6,740,113 B2 | 5/2004 | Vrba | |
| 6,746,464 B1 | 6/2004 | Makower | |
| 6,780,157 B2 | 8/2004 | Stephens et al. | |
| 6,795,188 B2 | 9/2004 | Ruck et al. | |
| 6,795,196 B2 | 9/2004 | Funakawa | |
| 6,798,522 B2 | 9/2004 | Stolte et al. | |
| 6,822,798 B2 | 11/2004 | Wu et al. | |
| 6,830,559 B2 | 12/2004 | Schock | |
| 6,832,024 B2 | 12/2004 | Gerstenberger et al. | |
| 6,842,639 B1 | 1/2005 | Winston et al. | |
| 6,847,449 B2 | 1/2005 | Bashkansky et al. | |
| 6,855,115 B2 | 2/2005 | Fonseca et al. | |
| 6,856,138 B2 | 2/2005 | Bohley | |
| 6,856,400 B1 | 2/2005 | Froggatt | |
| 6,856,472 B2 | 2/2005 | Herman et al. | |
| 6,860,867 B2 | 3/2005 | Seward et al. | |
| 6,866,670 B2 | 3/2005 | Rabiner et al. | |
| 6,878,113 B2 | 4/2005 | Miwa et al. | |
| 6,886,411 B2 | 5/2005 | Kjellman et al. | |
| 6,891,984 B2 | 5/2005 | Petersen et al. | |
| 6,895,106 B2 | 5/2005 | Wang et al. | |
| 6,898,337 B2 | 5/2005 | Averett et al. | |
| 6,900,897 B2 | 5/2005 | Froggatt | |
| 6,912,051 B2 | 6/2005 | Jensen | |
| 6,916,329 B1 * | 7/2005 | Zhao | 606/189 |
| 6,922,498 B2 | 7/2005 | Shah | |
| 6,937,346 B2 | 8/2005 | Nebendahl et al. | |
| 6,937,696 B1 | 8/2005 | Mostafavi | |
| 6,943,939 B1 | 9/2005 | DiJaili et al. | |
| 6,947,147 B2 | 9/2005 | Motamedi et al. | |
| 6,947,787 B2 | 9/2005 | Webler | |
| 6,949,094 B2 | 9/2005 | Yaron | |
| 6,952,603 B2 | 10/2005 | Gerber et al. | |
| 6,954,737 B2 | 10/2005 | Kalantar et al. | |
| 6,958,042 B2 | 10/2005 | Honda | |
| 6,961,123 B1 | 11/2005 | Wang et al. | |
| 6,966,891 B2 | 11/2005 | Ookubo et al. | 604/103.04 |
| 6,969,293 B2 | 11/2005 | Thai | |
| 6,969,395 B2 | 11/2005 | Eskuri | |
| 6,985,234 B2 | 1/2006 | Anderson | |
| 7,004,963 B2 | 2/2006 | Wang et al. | |
| 7,006,231 B2 | 2/2006 | Ostrovsky et al. | 356/479 |
| 7,010,458 B2 | 3/2006 | Wilt | |
| 7,024,025 B2 | 4/2006 | Sathyanarayana | |
| 7,027,211 B1 | 4/2006 | Ruffa | |
| 7,027,743 B1 | 4/2006 | Tucker et al. | |
| 7,033,347 B2 | 4/2006 | Appling | |
| 7,035,484 B2 | 4/2006 | Silberberg et al. | |
| 7,037,269 B2 | 5/2006 | Nix et al. | |
| 7,042,573 B2 | 5/2006 | Froggatt | |
| 7,044,915 B2 | 5/2006 | White et al. | 600/459 |
| 7,044,964 B2 | 5/2006 | Jang et al. | |
| 7,048,711 B2 | 5/2006 | Rosenman et al. | |
| 7,049,306 B2 | 5/2006 | Konradi et al. | |
| 7,058,239 B2 | 6/2006 | Singh et al. | |
| 7,060,033 B2 | 6/2006 | White et al. | |
| 7,060,421 B2 | 6/2006 | Naundorf et al. | |
| 7,063,679 B2 | 6/2006 | Maguire et al. | |
| 7,068,852 B2 | 6/2006 | Braica | |
| 7,074,188 B2 | 7/2006 | Nair et al. | |
| 7,095,493 B2 | 8/2006 | Harres | |
| 7,110,119 B2 | 9/2006 | Maestle | |
| 7,113,875 B2 | 9/2006 | Terashima et al. | |
| 7,123,777 B2 | 10/2006 | Rondinelli et al. | |
| 7,130,054 B2 | 10/2006 | Ostrovsky et al. | 356/479 |
| 7,139,440 B2 | 11/2006 | Rondinelli et al. | |
| 7,153,299 B1 | 12/2006 | Tu et al. | |
| 7,171,078 B2 | 1/2007 | Sasaki et al. | |
| 7,175,597 B2 | 2/2007 | Vince et al. | |
| 7,177,491 B2 | 2/2007 | Dave et al. | |
| 7,190,464 B2 | 3/2007 | Alphonse | |
| 7,215,802 B2 | 5/2007 | Klingensmith et al. | |
| 7,218,811 B2 | 5/2007 | Shigenaga et al. | |
| 7,236,812 B1 | 6/2007 | Ballerstadt et al. | |
| 7,245,125 B2 | 7/2007 | Harer et al. | |
| 7,245,789 B2 | 7/2007 | Bates et al. | |
| 7,249,357 B2 | 7/2007 | Landman et al. | |
| 7,289,842 B2 * | 10/2007 | Maschke | 600/478 |
| 7,291,146 B2 | 11/2007 | Steinke et al. | |
| 7,292,715 B2 | 11/2007 | Furnish | |
| 7,292,885 B2 | 11/2007 | Scott et al. | |
| 7,294,124 B2 | 11/2007 | Eidenschink | |
| 7,300,460 B2 | 11/2007 | Levine et al. | |
| 7,335,161 B2 | 2/2008 | Von Arx et al. | |
| 7,337,079 B2 | 2/2008 | Park et al. | |
| 7,355,716 B2 | 4/2008 | de Boer et al. | |
| 7,356,367 B2 | 4/2008 | Liang et al. | |
| 7,358,921 B2 | 4/2008 | Snyder et al. | |
| 7,359,062 B2 | 4/2008 | Chen et al. | |
| 7,359,554 B2 | 4/2008 | Klingensmith et al. | |
| 7,363,927 B2 | 4/2008 | Ravikumar | |
| 7,366,376 B2 | 4/2008 | Shishkov et al. | |
| 7,382,949 B2 | 6/2008 | Bouma et al. | |
| 7,387,636 B2 | 6/2008 | Cohn et al. | |
| 7,391,520 B2 | 6/2008 | Zhou et al. | |
| 7,397,935 B2 | 7/2008 | Kimmel et al. | |
| 7,399,095 B2 | 7/2008 | Rondinelli | |
| 7,408,648 B2 | 8/2008 | Kleen et al. | |
| 7,414,779 B2 | 8/2008 | Huber et al. | |
| 7,440,087 B2 | 10/2008 | Froggatt et al. | |
| 7,447,388 B2 | 11/2008 | Bates et al. | |
| 7,449,821 B2 | 11/2008 | Dausch | |
| 7,450,165 B2 | 11/2008 | Ahiska | |
| RE40,608 E | 12/2008 | Glover et al. | |
| 7,458,967 B2 | 12/2008 | Appling et al. | |
| 7,463,362 B2 | 12/2008 | Lasker et al. | |
| 7,463,759 B2 | 12/2008 | Klingensmith et al. | |
| 7,491,226 B2 | 2/2009 | Palmaz et al. | |
| 7,515,276 B2 | 4/2009 | Froggatt et al. | |
| 7,527,594 B2 | 5/2009 | Vardi et al. | |
| 7,534,251 B2 | 5/2009 | WasDyke | |
| 7,535,797 B2 | 5/2009 | Peng et al. | |
| 7,547,304 B2 | 6/2009 | Johnson | |
| 7,564,949 B2 | 7/2009 | Sattler et al. | |
| 7,577,471 B2 | 8/2009 | Camus et al. | |
| 7,583,857 B2 | 9/2009 | Xu et al. | |
| 7,603,165 B2 | 10/2009 | Townsend et al. | |
| 7,612,773 B2 | 11/2009 | Magnin et al. | |
| 7,633,627 B2 | 12/2009 | Choma et al. | |
| 7,645,229 B2 | 1/2010 | Armstrong | |
| 7,658,715 B2 | 2/2010 | Park et al. | |
| 7,660,452 B2 | 2/2010 | Zwirn et al. | |
| 7,660,492 B2 | 2/2010 | Bates et al. | |
| 7,666,204 B2 | 2/2010 | Thornton et al. | |
| 7,672,790 B2 | 3/2010 | McGraw et al. | |
| 7,680,247 B2 | 3/2010 | Atzinger et al. | |
| 7,684,991 B2 | 3/2010 | Stohr et al. | |
| 7,711,413 B2 | 5/2010 | Feldman et al. | |
| 7,720,322 B2 | 5/2010 | Prisco | |
| 7,728,986 B2 | 6/2010 | Lasker et al. | |
| 7,734,009 B2 | 6/2010 | Brunner et al. | |
| 7,736,317 B2 | 6/2010 | Stephens et al. | |
| 7,742,795 B2 | 6/2010 | Stone et al. | |
| 7,743,189 B2 | 6/2010 | Brown et al. | |
| 7,762,954 B2 | 7/2010 | Nix et al. | |
| 7,766,896 B2 | 8/2010 | Kornkven Volk et al. | |
| 7,773,792 B2 | 8/2010 | Kimmel et al. | |
| 7,775,981 B1 | 8/2010 | Guracar et al. | |
| 7,777,399 B2 | 8/2010 | Eidenschink et al. | |
| 7,781,724 B2 | 8/2010 | Childers et al. | |
| 7,783,337 B2 | 8/2010 | Feldman et al. | |
| 7,787,127 B2 | 8/2010 | Galle et al. | |
| 7,792,342 B2 | 9/2010 | Barbu et al. | |
| 7,801,343 B2 | 9/2010 | Unal et al. | |
| 7,801,590 B2 | 9/2010 | Feldman et al. | |
| 7,813,609 B2 | 10/2010 | Petersen et al. | |
| 7,831,081 B2 | 11/2010 | Li | |

(56) References Cited

U.S. PATENT DOCUMENTS

| | | |
|---|---|---|
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. ............ 600/585 |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1* | 4/2003 | Hamm et al. ............ 385/72 |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |

(56) References Cited

U.S. PATENT DOCUMENTS

| | | |
|---|---|---|
| 2004/0092830 A1 | 5/2004 | Scott et al. .................. 600/478 |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1* | 12/2004 | Brister et al. ................ 600/407 |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke ...................... 600/427 |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. ................ 600/434 |
| 2006/0067620 A1 | 3/2006 | Shishkov et al. |
| 2006/0072808 A1 | 4/2006 | Grimm et al. |
| 2006/0074318 A1* | 4/2006 | Ahmed et al. ................ 600/465 |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1* | 6/2006 | Webler ........................ 600/431 |
| 2006/0142703 A1 | 6/2006 | Carter et al. .................. 604/264 |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee .............................. 606/1 |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1* | 11/2006 | Maschke ...................... 600/1 |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1* | 12/2006 | Khamene et al. ............ 600/416 |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. .................... 600/459 |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. ................ 600/443 |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke ...................... 600/424 |
| 2007/0066890 A1 | 3/2007 | Maschke ...................... 600/424 |
| 2007/0066983 A1 | 3/2007 | Maschke ...................... 606/159 |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0167813 A1* | 7/2007 | Lee ............................. A61B 8/12 600/459 |
| 2007/0179487 A1* | 8/2007 | Tearney .................. A61B 5/0066 606/15 |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0244391 A1* | 10/2007 | Hirota .................. A61B 5/0066 600/443 |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1* | 2/2008 | Furnish ........................ 600/478 |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner ......................... 600/425 |
| 2008/0101667 A1 | 5/2008 | Begelman et al. |
| 2008/0108867 A1 | 5/2008 | Zhou |

(56) References Cited

U.S. PATENT DOCUMENTS

| | | |
|---|---|---|
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. ............... 600/467 |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1* | 9/2008 | Ilegbusi et al. ............... 600/479 |
| 2008/0247622 A1 | 10/2008 | Aylward et al. |
| 2008/0247716 A1* | 10/2008 | Thomas et al. ............... 385/101 |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9* | 6/2009 | Maschke ................ 600/424 |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1* | 8/2009 | Papaioannou et al. ........ 600/421 |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoke et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |

(56) References Cited

U.S. PATENT DOCUMENTS

| | | |
|---|---|---|
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | | |
|---|---|---|---|
| EP | 2178442 A1 | 4/2010 | |
| EP | 2438877 A2 | 4/2012 | |
| GB | 2280261 A | 1/1995 | |
| JP | 2000-037355 A | 2/2000 | |
| JP | 2000-262461 A | 9/2000 | |
| JP | 2000-292260 A | 10/2000 | |
| JP | 2000-329534 A | 11/2000 | |
| JP | 2001-125009 A | 5/2001 | |
| JP | 2001-272331 A | 10/2001 | |
| JP | 2002-503134 A | 1/2002 | |
| JP | 2002-088660 A | 3/2002 | |
| JP | 2002-523162 A | 7/2002 | |
| JP | 2002-374034 A | 12/2002 | |
| JP | 2003-143783 A | 5/2003 | |
| JP | 2003-172690 A | 6/2003 | |
| JP | 2003-256876 A | 9/2003 | |
| JP | 2003-287534 A | 10/2003 | |
| JP | 2004-004080 A | 1/2004 | |
| JP | 2004-510132 A | 4/2004 | |
| JP | 2004-528111 A | 9/2004 | |
| JP | 2005-274380 A | 10/2005 | |
| JP | 2005-533610 A | 11/2005 | |
| JP | 2006-184284 A | 7/2006 | |
| JP | 2006-266797 A | 10/2006 | |
| JP | 2006-313158 A | 11/2006 | |
| JP | 2007-510143 A | 4/2007 | |
| JP | 2009-233001 A | 10/2009 | |
| JP | 2009-536425 A | 10/2009 | |
| JP | 2010-516302 A | 5/2010 | |
| JP | 2010-516304 A | 5/2010 | |
| JP | 2011-056786 A | 3/2011 | |
| JP | 2011-508677 A | 3/2011 | |
| JP | 2013-546256 A | 12/2013 | |
| JP | 2014-501163 A | 1/2014 | |
| JP | 2014-506806 A | 3/2014 | |
| WO | 91/01156 A1 | 2/1991 | |
| WO | 92/16865 A1 | 10/1992 | |
| WO | 93/06213 A1 | 4/1993 | |
| WO | 93/08829 A1 | 5/1993 | |
| WO | 1998/38907 A1 | 9/1998 | |
| WO | 1998/57583 A1 | 12/1998 | |
| WO | 00/11511 A1 | 3/2000 | |
| WO | 2000/11511 A1 | 3/2000 | |
| WO | 2000/044296 A1 | 8/2000 | |
| WO | 2001/11409 A2 | 2/2001 | |
| WO | 2003/032936 A1 | 4/2003 | |
| WO | 2003/062802 A2 | 7/2003 | |
| WO | 03/073950 A1 | 9/2003 | |
| WO | 2004/010856 A1 | 2/2004 | |
| WO | WO 2004/023992 | 3/2004 | ............... A61B 5/00 |
| WO | 2004/096049 A2 | 11/2004 | |
| WO | 2005/047813 A1 | 5/2005 | |
| WO | 2005/106695 A1 | 11/2005 | |
| WO | 2006/016434 A1 | 2/2006 | |
| WO | 2006/029634 A2 | 3/2006 | |
| WO | 2006/037132 A1 | 4/2006 | |
| WO | 2006/039091 A2 | 4/2006 | |
| WO | 2006/061829 A1 | 6/2006 | |
| WO | 2006/068875 A2 | 6/2006 | |
| WO | 2006/111704 A1 | 10/2006 | |
| WO | 2006/119416 A1 | 11/2006 | |
| WO | 2006/121851 A2 | 11/2006 | |
| WO | WO 2006/119416 | 11/2006 | ............. G01S 15/89 |
| WO | 2006/130802 A2 | 12/2006 | |
| WO | 2007/002685 A2 | 1/2007 | |
| WO | WO 2007/025230 | 3/2007 | ............... A61B 8/12 |
| WO | 2007/045690 A1 | 4/2007 | |
| WO | 2007/058895 A2 | 5/2007 | |
| WO | 2007/060973 A1 | 5/2007 | |
| WO | 2007/067323 A2 | 6/2007 | |
| WO | 2007/084995 A2 | 7/2007 | |
| WO | 2008/058084 A2 | 5/2008 | |
| WO | 2008/069991 A1 | 6/2008 | |
| WO | 2008/107905 A2 | 9/2008 | |
| WO | 2009/009799 A1 | 1/2009 | |
| WO | 2009/009801 A1 | 1/2009 | |
| WO | 2009/046431 A1 | 4/2009 | |

(56) References Cited

FOREIGN PATENT DOCUMENTS

| | | |
|---|---|---|
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

Herz et al., "Micromotor endoscope catheter for in vivo, ultrahigh resolution optical coherence tomography", Optics Letters, Oct. 2004.*

Yaqoob et al., "Methods and application areas of endoscopic optical coherence tomography", J. Biomedical Optics, Nov./Dec. 2006.*

U.S. Appl. No. 60/949,472, Kemp et al., filed Jul. 12, 2007.

U.S. Appl. No. 60/949,511, Dick et al., filed Jul. 12, 2007.

Atlantis (TM) SR Pro Coronary Imaging Catheter 40 MHz Directions for Use, REF Catalog No. 38942 (published 2006), Boston Scientific Corporation, One Boston Scientific Place, Natick, MA 01760-1537 USA.

Davies et al. Plaque fissuring—the cause of acute myocardial infarction, sudden ischaemic death, and crescendo angina. British Heart Journal (1985) 53: 363-373.

Davies et al. Risk of thrombosis in human atherosclerotic plaques: role of extracellular lipid, macrophage, and smooth muscle cell content. British Heart Journal (1993) 69:377-381.

Jang et al. Visualization of Coronary Atherosclerotic Plaques in Patients Using Optical Coherence Tomography: Comparison With Intravascular Ultrasound. Journal of the American College of Cardiology (2002) 39:604-609.

Little et al. The underlying coronary lesion in myocardial infarction: implications for coronary angiography. Clinical Cardiology (1991) 14(11):868-874. Abstract Only.

Nissen. Coronary Angiography and Intravascular Ultrasound. American Journal of Cardiology (2001) 87(suppl):15A-20A.

Princetel, Inc. R-series Fiber Optic Rotary Joint data sheet. www.princetel.com (accessed May 18, 2007) Princetel, Inc., 4 Princess Rd, Ste 209, Lawrenceville, NJ 08648.

Rabbani et al. Review: Strategies to achieve coronary arterial plaque stabilization. Cardiovascular Research. (1999) 41:402-417.

Yaqoob et al. Methods and application areas of endoscopic optical coherence tomography. Journal of Biomedical Optics (2006) 11(6): 063001-1-063001-19.

Strickland, 1970, Time-Domain Reflectometer Measurements, Tektronix, Beaverton, OR, (107 pages).

Tonino et al., 2009, Fractional flow reserve versus angiography for guiding percutaneous coronary intervention, The New England Journal of Medicine, 360:213-224.

Toregeani et al., 2008, Evaluation of hemodialysis arteriovenous fistula maturation by color-flow Doppler ultrasound, J Vasc. Bras. 7(3):203-213.

Traunecker et al., 1991, Bispecific single chain molecules (Janusins) target cytotoxic lymphocytes on HIV infected cells EMBO J., 10:3655-3659.

Trolier-McKinstry et. al., 2004, Thin Film Piezoelectric for MEMS, Journal of Electroceramics 12:7-17.

Tuniz et al., 2010, Weaving the invisible thread: design of an optically invisible metamaterial fibre, Optics Express 18(17):18095-18105.

Urban et al., 2010, Design of a Pressure Sensor Based on Optical Bragg Grating Lateral Deformation, Sensors (Basel), 10(12):11212-11225.

Vakoc et al., 2005, Phase-Resolved Optical Frequency Domain Imaging, Optics Express 13(14):5483-5493.

Wang et al., 2006, Multiple biomarkers for the prediction of first major cardiovascular events and death, The New England Journal of Medicine, 355(25):2631-2639.

Villard et al., 2002, Use of a blood substitute to determine instantaneous murine right ventricular thickening with optical coherence tomography, Circulation, 105:1843-1849.

Forstner & Moonen, 1999, A metric for covariance matrices, In Technical Report of the Dpt of Geodesy and Geoinformatics, Stuttgart University, 113-128.

Waterhouse et. al., 1993, Combinatorial infection and in vivo recombination: a strategy for making large phage antibody repertoires, Nucleic Acids Res., 21:2265-2266.

Yasuno et al., 2004, Polarization-sensitive complex Fourier domain optical coherence tomography for Jones matrix imaging of biological samples, Applied Physics Letters 85(15):3023-3025.

Zhang et al., 2004, Full range polarization-sensitive Fourier domain optical coherence tomography, Optics Express, 12(24):6033-6039.

Fatemi et al., 1999, Vibro-acoustography: an imaging modality based on ultrasound-stimulated acoustic emission, PNAS U.S.A., 96(12):6603-6608

Griffiths et al., 1993, Human anti-self antibodies with high specificity from phage display libraries, The EMBO Journal, 12:725-734.

Harrison et al., 2011, Guidewire Stiffness: What's in a name?, J Endovasc Ther, 18(6):797-801.

Rollins et al., 1998, In vivo video rate optical coherence tomography, Optics Express 3:219-229.

Zitova et al., 2003, Image registration methods: A survey. Image and Vision Computing, 21(11):977-1000.

Wegener, 2011, 3D Photonic Metamaterials and Invisibility Cloaks: The Method of Making, MEMS 2011, Cancun, Mexico, Jan. 23-27, 2011.

Jiang et al., 1992, Image registration of multimodality 3-D medical images by chamfer matching, Proc. SPIE 1660, Biomedical Image Processing and Three-Dimensional Microscopy, 356-66.

Bouma et al., 1999, Power-efficient nonreciprocal interferometer and linear-scanning fiber-optic catheter for optical coherence tomography, Optics Letters, 24(8):531-533.

Blanchet et al., 1993, Laser Ablation and the Production of Polymer Films, Science, 262(5134):719-721.

Li et al., 2000, Optical Coherence Tomography: Advanced Technology for the Endoscopic Imaging of Barrett's Esophagus, Endoscopy, 32(12):921-930.

Bruining et al., 2009, Intravascular Ultrasound Registration/ Integration with Coronary Angiography, Cardiology Clinics, 27(3):531-540.

Clarke et al., 1995, Hypoxia and myocardial ischaemia during peripheral angioplasty, Clinical Radiology, 50(5):301-303.

David et al., 1974, Protein iodination with solid-state lactoperoxidase, Biochemistry 13:1014-1021.

Adler et al., 2007, Phase-Sensitive Optical Coherence Tomography at up to 370,000 Lines Per Second Using Buffered Fourier Domain Mode-Locked Lasers, Optics Letters, 32(6):626-628.

Elghanian et al., 1997, Selective colorimetric detection of polynucleotides based on the distance-dependent optical properties of gold nanoparticles, Science, 277(5329):1078-1080.

Gould et al., 1974, Physiologic basis for assessing critical coronary stenosis, American Journal of Cardiology, 33:87-94.

Tearney et al., 1997, In vivo Endoscopic Optical Biopsy with Optical Coherence Tomography, Science, 276:2037-2039.

Brummer, 1997, An euclidean distance measure between covariance matrices of speechcepstra for text-independent speaker recognition, in Proc. South African Symp. Communications and Signal Processing:167-172.

(56) References Cited

OTHER PUBLICATIONS

Jakobovits et al., 1993, Germ-line transmission and expression of a human-derived yeast artificial chromosome, Nature 362:255-258.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Barnea et al., 1972, A class of algorithms for fast digital image registration, IEEE Trans. Computers, 21(2):179-186.
Sihan et al., 2008, a novel approach to quantitative analysis of intraluminal optical coherence tomography imaging, Comput. Cardiol:1089-1092.
Karapatis et al., 1998, Direct rapid tooling:a review of current research, Rapid Prototyping Journal, 4(2):77-89.
Kozbor et al., 1984, A human hybrid myeloma for production of human monoclonal antibodies, J. Immunol., 133:3001-3005.
Larin et al., 2004, Measurement of Refractive Index Variation of Physiological Analytes using Differential Phase OCT, Proc of SPIE 5325:31-34.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Lefevre et al., 2001, Stenting of bifurcation lesions:a rational approach, J. Interv. Cardiol., 14(6):573-585.
Fischler et al., 1973, The representation and matching of pictorial structures, IEEE Transactions on Computer 22:67-92.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Nitenberg et al., 1995, Coronary vascular reserve in humans: a critical review of methods of evaluation and of interpretation of the results, Eur Heart J. 16(Suppl 1):7-21.
Oesterle et al., 1986, Angioplasty at coronary bifurcations: single-guide, two-wire technique, Cathet Cardiovasc Diagn., 12:57-63.
Oldenburg et al., 2003, Fast-Fourier-Domain Delay Line for In Vivo Optical Coherence Tomography with a Polygonal Scanner, Applied Optics, 42(22):4606-4611.
Pain et al., 1981, Preparation of protein A-peroxidase mono conjugate using a heterobifunctional reagent, and its use in enzyme immunoassays, J Immunol Methods, 40:219-30.
Persson et al., 1985, Acoustic impedance matching of medical ultrasound transducers, Ultrasonics, 23(2):83-89.
Kersey et al., 1991, Polarization insensitive fiber optic Michelson interferometer, Electron. Lett. 27:518-520.
Mindlin et al., 1936, A force at a point of a semi-infinite solid, Physics, 7:195-202.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Munson et al., 1980, Ligand: a versatile computerized approach for characterization of ligand-binding systems, Analytical Biochemistry, 107:220-239.
Smith et al., 1989, Absolute displacement measurements using modulation of the spectrum of white light in a Michelson interferometer, Applied Optics, 28(16):3339-3342.
Milstein et al., 1983, Hybrid hybridomas and their use in immunohistochemistry, Nature 305:537-540.
Soller, 2003, Polarization diverse optical frequency domain interferometry:All coupler implementation, Bragg Grating, Photosensitivity, and Poling in Glass Waveguides Conference MB4:30-32.
Stenqvist et al., 1983, Stiffness of central venous catheters, Acta Anaesthesiol Scand., 2:153-157.
Sutcliffe et al., 1986, Dynamics of UV laser ablation of organic polymer surfaces, Journal of Applied Physics, 60(9):3315-3322.
Vakhtin et al., 2003, Common-path interferometer for frequency-domain optical coherence tomography, Applied Optics, 42(34):6953-6958.
Verhoeyen et al., 1988, Reshaping human antibodies: grafting an antilysozyme activity, Science, 239:1534-1536.
Wang et al., 2009, Robust Guidewire Tracking in Fluoroscopy, IEEE Conference on Computer Vision and Pattern Recognition—CVPR 2009:691-698.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Felzenszwalb et al., 2005, Pictorial Structures for Object Recognition, International Journal of Computer Vision, 61(1):55-79.
Juviler et al., 2008, Anorectal sepsis and fistula-in-ano, Surgical Technology International, 17:139-149.
Kirkman, 1991, Technique for flow reduction in dialysis access fistulas, Surg Gyn Obstet, 172(3):231-3.
Wyawahare et al., 2009, Image registration techniques: an overview, International Journal of Signal Processing, Image Processing and Pattern Recognition, 2(3):11-28.
Suzuki, 2013, A novel guidewire approach for handling acute-angle bifurcations, J Inv Cardiol 25(1):48-54.
West et al., 1991, Arterial insufficiency in hemodialysis access procedures: correction by banding technique, Transpl Proc 23(2):1838-40.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
International Search Report and Written Opinion dated Jul. 30, 2014, for International Patent Application No. PCT/US14/21659, filed Mar. 7, 2014 (15 pages).
Amini et al., 1990, Using dynamic programming for solving variational problems in vision, IEEE Transactions on Pattern Analysis and Machine Intelligence, 12(9):855-867.
Abdi et al., 2010, Principal component analysis, Wiley Interdisciplinary Reviews: Computational Statistics 2:433-459.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Bain, 2011, Privacy protection and face recognition, Chapter 3, Handbook of Face Recognition, Stan et al., Springer-Verlag.
Breiman, 2001, Random forests, Machine Learning 45:5-32.
Burr et al., 2005, Searching for the Center of an Ellipse in Proceedings of the 17th Canadian Conference on Computational Geometry:260-263.
Fookes et al., 2002, Rigid and non-rigid image registration and its association with mutual information:A review, Technical Report ISBN:1 86435 569 7, RCCVA, QUT.
Cavalli et al., 2010, Nanosponge formulations as oxygen delivery systems, International Journal of Pharmaceutics 402:254-257.
Collins, 1993, Coronary flow reserve, British Heart Journal 69:279-281.

(56) References Cited

OTHER PUBLICATIONS

Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Ergun et al., 2003, Capacitive Micromachined Ultrasonic Transducers:Theory and Technology, Journal of Aerospace Engineering, 16(2):76-84.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Evans et al., 2006, Optical coherence tomography to identify intramucosa carcinoma and high-grade dysplasia in Barrett's esophagus, Clin Gast Hepat 4(1):38-43.
Grund et al., 2010, Analysis of biomarker data:logs, odds, ratios and ROC curves, Curr Opin HIV AIDS 5(6):473-479.
Gotzinger et al., 2005, High speed spectral domain polarization sensitive optical coherence tomography of the human retina, Optics Express 13(25):10217-10229.
Griffiths et al., 1994, Isolation of high affinity human antibodies directly from large synthetic repertoires, The EMBO Journal, 13(14):3245-3260.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
Bonnema, 2008, Imaging Tissue Engineered Blood Vessel Mimics with Optical Tomography, College of Optical Sciences dissertation, University of Arizona (252 pages).
International Search Report and Written Opinion dated Nov. 2, 2012, for International Patent Application No. PCT/US12/53168, filed Aug. 30, 2013 (8 pages).
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).
International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
International Search Report and Written Opinion dated Jan. 16, 2009, for International Patent Application No. PCT/US08/78963 filed on Oct. 6, 2008 (7 Pages).
Wang et al., 2011, In vivo intracardiac optical coherence tomography imaging through percutaneous access: toward image-guided radio-frequency ablation, J. Biomed. Opt. 0001 16(11):110505-1 (3 pages).
Canny, 1986, A computational approach to edge detection, IEEE Trans. Pattern Anal. Mach. Intell. 8:679-698.
Maintz et al., 1998, An Overview of Medical Image Registration Methods, Technical Report UU-CS, (22 pages).
Jakobovits et al., 1993, Analysis of homozygous mutant chimeric mice:deletion of the immunoglobulin heavy-chain joining region blocks B-cell development and antibody production, PNAS USA 90:2551-255.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Karp et al., 2009, The benefit of time-of-flight in PET imaging, J Nucl Med 49:462-470.

(56) References Cited

OTHER PUBLICATIONS

Kelly et al., 2005, Detection of Vascular Adhesion Molecule-1 Expression Using a Novel Multimodal Nanoparticle, Circulation Research 96:327-336.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Larin et al., 2002, Noninvasive Blood Glucose Monitoring with Optical Coherence Tomography: a pilot study in human subjects, Diabetes Care, 25(12):2263-7.
Brown, 1992, A survey of image registration techniques, ACM Computing Surveys 24(4):325-376.
Loo, 2004, Nanoshell Enabled Photonics-Based Imaging and Therapy of Cancer, Technology in Cancer Research & Treatment 3(1):33-40.
Turk et al., 1991, Eigenfaces for Recognition, Journal of Cognitive Neuroscience 3(1):71-86.
Choma et al., 2003, Sensitivity Advantage of Swept Source and Fourier Domain Optical Coherence Tomography, Optics Express 11(18):2183-2189.
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Mendieta et al., 1996, Complementary sequence correlations with applications to reflectometry studies, Instrumentation and Development 3(6):37-46.
Mickley, 2008, Steal Syndrome—strategies to preserve vascular access and extremity, Nephrol Dial Transplant 23:19-24.
Goel et al., 2006, Minimally Invasive Limited Ligation Endoluminal-assisted Revision (MILLER) for treatment of dialysis access-associated steal syndrome, Kidney Int 70(4):765-70.
Miller et al., 2010, The MILLER banding procedure is an effective method for treating dialysis-associated steal syndrome, Kidney International 77:359-366.
Morrison et al., 1984, Chimeric human antibody molecules: mouse antigen-binding domains with human constant region domains, PNAS 81:6851-6855.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Nygren, 1982, Conjugation of horseradish peroxidase to Fab fragments with different homobifunctional and heterobifunctional cross-linking reagents. A comparative study, J. Histochem. and Cytochem. 30:407-12.
Tuzel et al., 2006, Region Covariance: A Fast Descriptor for Detection and Classification, European Conference on Computer Vision (ECCV).
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Bail et al., 1996, Optical coherence tomography with the "Spectral Radar"—Fast optical analysis in volume scatterers by short coherence interferometry, Optics Letters 21(14):1087-1089.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Placht et al., 2012, Fast time-of-flight camera based surface registration for radiotherapy patient positioning, Medical Physics 39(1):4-17.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Robbin et al., 2002, Hemodialysis Arteriovenous Fistula Maturity: US Evaluation, Radiology 225:59-64.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Siwy et al., 2003, Electro-responsive asymmetric nanopores in polyimide with stable ion-current signal, Applied Physics A: Materials Science & Processing 76:781-785.
Smith, 1997, The Scientist and Engineer's Guide to Digital Signal Processing, California Technical Publishing, San Diego, CA:432-436.
Nezam, 2008, High Speed Polygon-Scanner-Based Wavelength-Swept Laser Source in the Telescope-Less Configurations with Application in Optical Coherence Tomography, Optics Letters 33(15):1741-1743.
Song et al., 2012, Active tremor cancellation by a "Smart" handheld vitreoretinal microsurgical tool using swept source optical coherence tomography, Optics Express, 20(21):23414-23421.
Strobl et al., 2009, An Introduction to Recursive Partitioning:Rationale, Application and Characteristics of Classification and Regression Trees, Bagging and Random Forests, Psychol Methods., 14(4):323-348.

\* cited by examiner

OCT-IVUS CATHETER FOR CONCURRENT LUMINAL IMAGING

CROSS-REFERENCE TO RELATED INVENTIONS

This application claims priority pursuant to 35 U.S.C. § 119(e) from U.S. Provisional Application Ser. Nos. 60/949,472 and 60/949,511, both filed Jul. 12, 2007 and incorporated by reference herein.

BACKGROUND OF THE INVENTION

The present invention relates generally to an apparatus for in vivo imaging. More particularly, the present invention relates to a catheter that incorporates an Optical Coherence Tomography (OCT) system and an Intravascular Ultrasound (IVUS) system for concurrent imaging of luminal systems, such as imaging the vasculature system, including, without limitation, cardiac vasculature, peripheral vasculature and neural vasculature.

Myocardial infarction or heart attack remains the leading cause of death in society. Until recently, many investigators believed that the primary mechanism for myocardial infarction was coronary arteries critically blocked with atherosclerotic plaque that subsequently progressed to total occlusion. Recent evidence from many investigational studies, however, clearly indicates that most infarctions are caused by sudden rupture of non-critically stenosed coronary arteries resulting from sudden plaque rupture. For example, Little et al. (Little, W C, Downes, T R, Applegate, R J. The underlying coronary lesion in myocardial infarction: implications for coronary angiography. *Clin Cardiol* 1991, 14: 868-874, incorporated by reference herein) observed that approximately 70% of patients suffering from an acute plaque rupture were initiated on plaques that were less than 50% occluded as revealed by previous coronary angiography. This and similar observations have been confirmed by other investigators (Nissen, S. Coronary angiography and intravascular ultrasound. *Am J Cardiol* 2001, 87 (suppl): 15A-20 A, incorporated by reference herein).

The development of technologies to identify these unstable plaques holds the potential to decrease substantially the incidence of acute coronary syndromes that often lead to premature death. Unfortunately, no methods are currently available to the cardiologist that may be applied to specify which coronary plaques are vulnerable and thus prone to rupture. Although treadmill testing has been used for decades to identify patients at greater cardiovascular risk, this approach does not have the specificity to differentiate between stable and vulnerable plaques that are prone to rupture and frequently result in myocardial infarction. Inasmuch as a great deal of information exists regarding the pathology of unstable plaques (determined at autopsy), technologies based upon identifying the well-described pathologic appearance of the vulnerable plaque offers a promising long term strategy to solve this problem.

The unstable plaque was first identified and characterized by pathologists in the early 1980's. Davis noted that with the reconstruction of serial histological sections in patients with acute myocardial infarctions associated with death, a rupture or fissuring of athermanous plaque was evident (Davis M J, Thomas A C. Plaque fissuring: the cause of acute myocardial infarction, sudden death, and crescendo angina. *Br Heart J* 1985; 53: 3 63-37 3, incorporated by reference herein). Ulcerated plaques were further characterized as having a thin fibrous cap, increased macrophages with decreased smooth muscle cells and an increased lipid core when compared to non-ulcerated atherosclerotic plaques in human aortas (Davis M J, Richardson E D, Woolf N. Katz O R, Mann J. Risk of thrombosis in human atherosclerotic plaques: role of extracellular lipid, macrophage, and smooth muscle cell content, incorporated by reference herein). Furthermore, no correlation in size of lipid pool and percent stenosis was observed when imaging by coronary angiography. In fact, most cardiologists agree that unstable plaques progress to more stenotic yet stable plaques through progression via rupture with the formation of a mural thrombus and plaque remodeling, but without complete luminal occlusion (Topol E J, Rabbaic R. Strategies to achieve coronary arterial plaque stabilization. *Cardiovasc Res* 1999; 41: 402-417, incorporated by reference herein). Neovascularization with intra-plaque hemorrhage may also play a role in this progression from small lesions, i.e., those less than about 50% occluded, to larger significant plaques. Yet, if the unique features of unstable plaque could be recognized by the cardiologist and then stabilized, a dramatic decrease may be realized in both acute myocardial infarction and unstable angina syndromes, and in the sudden progression of coronary artery disease.

The present invention uses depth-resolved light reflection or Optical Coherence Tomography to identify the pathological features that have been identified in the vulnerable plaque. In OCT, light from a broad band light source or tunable laser source is split by an optical fiber splitter with one fiber directing light to the vessel wall and the other fiber directing light to a reference mirror. The distal end of the optical fiber is interfaced with a catheter for interrogation of the coronary artery during a heart catheterization procedure. The reflected light from the plaque is recombined with the signal from the reference mirror forming interference fringes (measured by a photovoltaic detector) allowing precise depth-resolved imaging of the plaque on a micron scale.

OCT uses a superluminescent diode source or tunable laser source emitting a 400-2000 nm wavelength, with a 50-250 nm band width (distribution of wave length) to make in situ tomographic images with axial resolution of 2-20 µm and tissue penetration of 2-3 mm. OCT has the potential to image tissues at the level of a single cell. In fact, the inventors have recently utilized broader bandwidth optical sources so that axial resolution is improved to 4 um or less. With such resolution, OCT can be applied to visualize intimal caps, their thickness, and details of structure including fissures, the size and extent of the underlying lipid pool and the presence of inflammatory cells. Moreover, near infrared light sources used in OCT instrumentation can penetrate into heavily calcified tissue regions characteristic of advanced coronary artery disease. With cellular resolution, application of OCT may be used to identify other details of the vulnerable plaque such as infiltration of monocytes and macrophages. In short, application of OCT can provide detailed images of a pathologic specimen without cutting or disturbing the tissue.

An OCT catheter to image coronary plaques has been built and is currently being tested by investigators. (Jang I K, Bouma B E, Hang O H, et al. Visualization of coronary atherosclerotic plaques in patients using optical coherence tomography: comparison with intravascular ultrasound. *JACC* 2002; 3 9: 604-609, incorporated by reference herein). The prototype catheter consists of a single light source and is able to image over a 360 degree arc of a coronary arterial lumen by rotating a shaft that spins the optical fiber. Because the rotating shaft is housed outside of the body, the spinning rod in the catheter must rotate with uniform angular velocity so that the light can be focused for equal intervals of time on each angular segment of the coronary artery.

While OCT imaging provides high resolution (2-20 µm) tomographic visualization of coronary arteries, OCT, however, lacks penetration with a maximum penetration depth of only 2-3 mm into the tissue. The present invention overcomes this disadvantage by incorporating an ultrasound transducer suitable for performing intravascular ultrasound ("IVUS") into an OCT catheter to form an OCT-IVUS catheter. The present invention uses IVUS imaging to identify the pathological features that have been identified in the vulnerable plaque. A particularly valuable tool, IVUS technology uses high frequency sound waves to detect blood vessel blockages and other problems such as aneurysms.

Ultrasound imaging systems can be equipped with a 38 mm aperture, broadband (5-10 MHz) linear array transducer. Cells can be imaged in color power Doppler, power Doppler, M-mode and B-scan modes. B-scan sonogram images, also called the grayscale mode, are the typical ultrasound method to monitor or examine the human body using backscattering of acoustic waves. M-mode ultrasound employs a sequence of scans at a fixed ultrasound beam over a given time period. M-mode is used for visualizing rapidly moving subjects, such as heart valves. Compared to conventional B-scan images, Doppler ultrasound is used to assess changes in the frequency of reflected acoustic waves. Color power Doppler converts reflected acoustic waves that are Doppler shifted into colors that overlay the conventional B-scan images and can indicate the speed and direction of moving objects. Power Doppler ultrasound is most commonly used to evaluate moving objects and has higher sensitivity than the color power Doppler mode. The gain of the color power and Doppler imaging mode can be manually adjusted to suppress the background noise. If the settings of the ultrasound instrumentation remain unchanged, objective comparisons of each can be made. Additional disclosure explaining how OCT and ultrasound imaging systems work and cooperate can be found in commonly assigned and co-pending U.S. patent application Ser. No. 11/550,771, filed Oct. 18, 2006 and published as U.S. Publication No. US 2008-0097194 on Apr. 24, 2008, which is incorporated herein by reference in its entirety.

IVUS is a widely available clinical tool for guiding percutaneous interventions and/or intraluminal imaging. While IVUS uses frequencies from 20 to 40 MHz and provides good depth penetration, it lacks sufficient resolution (~120 µm) to study thin-cap thrombus or atheroma lesions and other fine details with the vasculature. Conversely, while OCT provides high resolution (2-20 µm) tomographic visualization of coronary arteries, OCT, however, lacks penetration with a maximum penetration depth of only 2-3 mm. However, it has been found that OCT can image behind calcifications clearly while ultrasounds are intensely reflected. The current high resolution capabilities of OCT are well suited for imaging vulnerable plaques but poor depth penetration hamper full characterization of coronary lesions and plaque burden. Because IVUS penetrates deeper into the media and adventitia, combining OCT and IVUS modalities will enhance quantitative analysis of coronary arteries significantly.

SUMMARY OF THE INVENTION

The present invention relates to a catheter that incorporates an Optical Coherence Tomography (OCT) system and an Intravascular Ultrasound ("IVUS") system for concurrent imaging of luminal systems, such as imaging the vasculature system, including, without limitation, cardiac vasculature, peripheral vasculature and neural vasculature. An OCT assembly and an IVUS transducer are positioned at the distal end of the catheter.

A combined OCT and IVUS catheter imaging system has been developed to provide cross-sectional structural images of blood vessels, including coronary arteries. A catheter assembly surrounding an OCT assembly and an IVUS transducer at the distal end of an imaging core is used to accomplish such imaging. The catheter assembly is positioned within a blood vessel at the site of interest (i.e., the location of a stenosis). The OCT assembly and IVUS transducer generate a series of pulses which are transmitted outward from the OCT assembly and the IVUS transducer as they are rotated. Echo pulses reflected from the surrounding tissues are received by the OCT assembly and the IVUS transducer and collected by a control apparatus coupled to the proximal end of the sheath. The collected data is then combined, transformed, and displayed as a cross-sectional image of the vessel and surrounding tissue.

The scope of the invention is indicated in the appended claims. It is intended that all changes or modifications within the meaning and range of equivalents are embraced by the claims.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PREFERRED EMBODIMENTS

Figure 1:
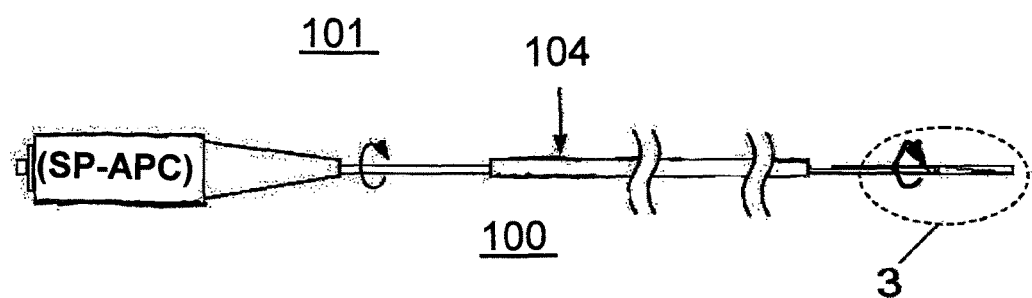
FIG. 1 is a diagrammatic side view of the present invention's OCT-IVUS system.

In the accompanying figures, like elements are identified by like reference numerals among the several preferred embodiments of the present invention.

In the present invention, a distal end assembly including an ultrasound transducer 120 and an optical coherence tomography ("OCT") assembly (as hereinafter described)

are positioned longitudinally adjacent or in close proximity to each other at or near a distal end of a catheter assembly 111. Both the ultrasound transducer 120 and the OCT assembly are coupled to a rotary drive system (as hereinafter described) that rotates both the OCT assembly and the ultrasound transducer 120 about their longitudinal axis and within a catheter sheath.

The ultrasound transducer 120 may be a single-element crystal or probe that is mechanically scanned or rotated back and forth to cover a sector over a selected angular range. OCT and acoustic signals are then transmitted and echoes (or backscatter) from these OCT and acoustic signals are received. The ultrasound transducer 120 and the OCT assembly may be oriented to direct their respective energies such that the optical signal and the ultrasound signal scan the same or at least partially overlapping spatial areas. Alternatively, the optical signal and the ultrasound signal may be aligned by employing appropriate computer processing software to adjust for spatial discrepancies between the two signals and permit simultaneous display of at least partially coordinated optical images and the ultrasound images to the physician. The backscatter data can be used to identify the type of a scanned tissue. As the probe is swept through the sector, many OCT and acoustic lines are processed building up a sector-shaped image of the patient. After the data is collected, an image (e.g., a combined OCT and IVUS image) of the blood vessel and any associated intraluminal structures, such as plaque, thrombus, stent, etc., can be reconstructed using well-known techniques. This image is then visually analyzed by a physician to assess the vessel components and plaque content.

Image analysis of data collected from use of the present invention includes determining the size of the lumen and amount of plaque in the vessel. This is performed by generating an image of the vessel (e.g., combined OCT and IVUS image) and manually drawing contoured boundaries on the image where the clinician believes the luminal and the medial-adventitial borders are located. In other words, the luminal border, which demarcates the blood-intima interface, and the medial-adventitial border, which demarcates the external elastic membrane or the boundary between the media and the adventitia, are manually drawn to identify the plaque-media complex that is located there between.

As illustrated generally in FIG. 1, the OCT-IVUS system 100 of present invention includes a proximal end and a distal end. The proximal end of the OCT-IVUS system 100 includes a rotary optical fiber connector 101, sometimes also referred to in the art as a fiber optical rotary joint ("FORJ"). The optical fiber connector 101 joins two optical fibers, one optical fiver 105 that is stationary and proximal to the optical fiber connector 101 and another optical fiber 106 that is rotatable and distal to the optical fiber connector 101. Different types of optical fiber connectors 101, e.g., SC-APC plug-in connector, have been developed in the art for various applications and are encompassed by the present invention. A distal end catheter assembly 111, shown in greater detail in FIG. 3, consists generally of the OCT assembly and the ultrasound transducer 120 positioned with a housing 110, that is coupled at its proximal end to a rotary drive shaft 104, that, in turn, is coupled to a rotary drive actuator, such as that illustrated in and described with reference to FIG. 2.

Figure 2:
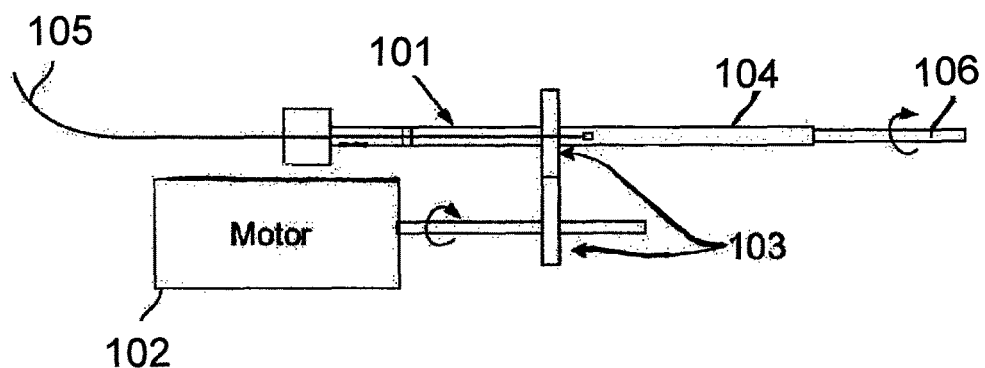
FIG. 2 is a side view of an actuation system for rotating the OCT-IVUS catheter in accordance with the present invention.

Turning to FIG. 2, a rotary actuation system, which includes a rotary motor 102, an optical fiber connector 101, and gears 103, is illustrated rotating a driveshaft 104. The driveshaft 104 itself is comprised of a fitting (not shown) that overlies and houses the optical fiber 106 distal to the optical fiber connector 101. This rotary actuation system may also include a linear actuation system (not shown) to facilitate manual or automated pull-back of the catheter.

Figure 3:
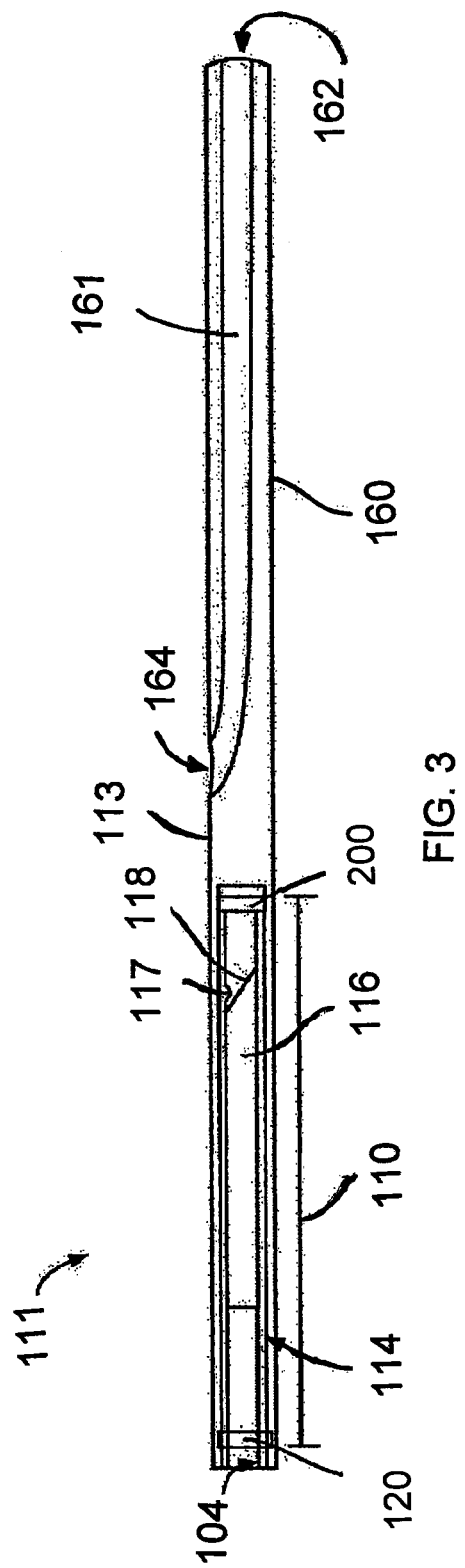
FIG. 3 is a side view of the distal end optics of the OCT assembly in accordance with the present invention taken from circle 3 in FIG. 1.

FIG. 3 provides a closer side view of the distal end of the OCT-IVUS system 100 depicted in FIG. 1. The catheter assembly 111 includes an outer catheter sheath 113 that terminates at a distal end thereof in a distal tip 200 having a guidewire lumen 161 configured for rapid guidewire exchange. The outer catheter sheath 113 is preferably at least partially, preferably near totally, transparent to both optical and ultrasound energy to permit transmission of optical and ultrasonic energy to and from the IVUS-OCT catheter assembly 111. Co-pending, commonly assigned U.S. Provisional Patent Application Ser. No. 60/949,511, filed Jul. 12, 2007, from which priority is claimed, describes a monolithic catheter construct and rotary drive system well-suited for use with the present invention, and is hereby incorporated by reference thereto as if fully set forth herein.

A driveshaft 104 extends from the proximal end of the OCT-IVUS system 100 into the catheter assembly 111. In one embodiment, the outer surface of the catheter assembly 111 is covered and protected by an outer sheath formed of PFA (perfluoroalkoxy). To avoid damage to blood vessels, sheaths may also be formed of other flexible plastic-type materials, having high hoop strengths or with reinforcements, to help stop this kinking and bending while reducing tissue damage during catheter introduction. Other appropriate materials known in the art for use as an outer sheath are also within the scope of the present invention.

The catheter assembly 111 includes, but is not limited to, a protection bearing 110, a ferrule 114, a GRIN lens assembly 116, a prism 118, an OCT imaging port 117, an optical fiber 106, and an IVUS transducer 120, all of which are housed within the protection bearing 110. The catheter assembly 111 may also include a rapid exchange section 160 which has a guidewire lumen 161 that extends between a guidewire entrance port 162 and a guidewire exit port 164. The protection bearing 110 serves as a shield for OCT and IVUS components. The protection bearing 110 has at least one transparent portion 117, which is preferably an opening through the protection bearing 110 that is transparent to both optical and ultrasound energy to permit transmission of such energy to and from the OCT assembly and the ultrasound transducer. The at least one transparent portion 117 may be positioned through a wall of the protection bearing 110 or through an end of the protection bearing 110.

Figure 4:
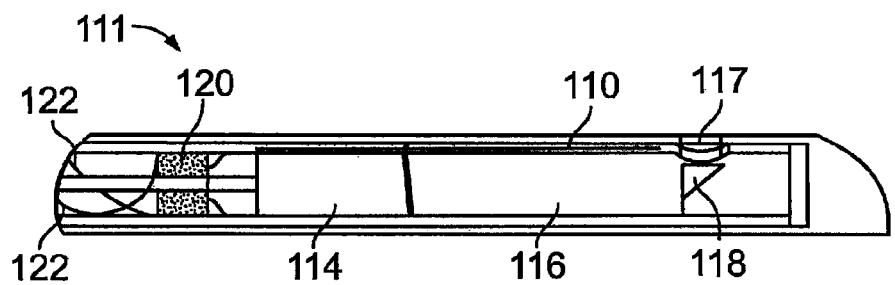
FIG. 4 is a side view of the distal end optics and ultrasound transducer of one embodiment of the invention.

FIG. 4 illustrates one embodiment of the invention, wherein an ultrasound transducer 120 is positioned proximal to the OCT assembly (i.e., ferrule 114, GRIN lens assembly 116, and prism 118). In this embodiment, the ultrasound transducer 120 possesses a cylindrical structure with a hollow core to provide access for an optical fiber 106 to pass through to the OCT assembly. Electrical conduits or wires 122 provide electrically couple the ultrasound transducer 120 to a power source (not shown) and to an ultrasound receiver (not shown).

Figure 5:
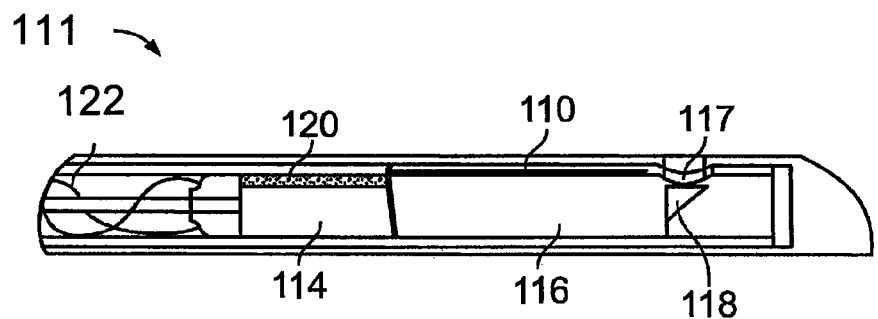
FIG. 5 is a side view of the distal end optics and ultrasound transducer of another embodiment of the invention.
Figure 6:
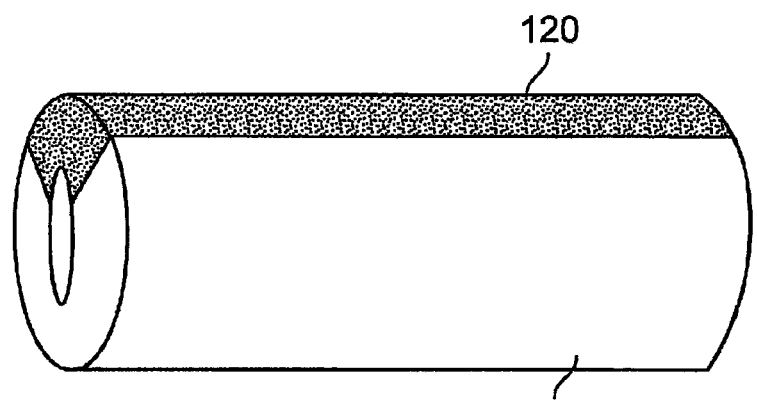
FIG. 6 is perspective view of a combined ferrule-ultrasound transducer in accordance with an embodiment of the present invention.

FIG. 5 illustrates another embodiment of the invention, wherein an ultrasound transducer 120 is formed on or as a part of the ferrule 114 of the OCT assembly. FIG. 6 provides a perspective view of the ferrule 114 with the ultrasound transducer 120 embedded with a wall of the ferrule 114. Similar to the embodiment illustrated in FIG. 4, in this embodiment, conduits or wires 122 provide power to the ultrasound transducer 120 and electrically connect the transducer to the ultrasound receiver (not shown).

Figure 7:
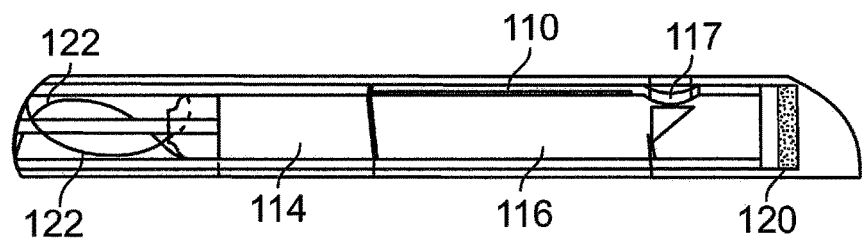
FIG. 7 is a side view of the distal end optics and ultrasound transducer of another embodiment of the invention.

FIG. 7 illustrates another embodiment of the invention, wherein the ultrasound transducer 120 is positioned distal to the OCT assembly and is generally forward-looking. In this embodiment, wires 122 extend across the OCT assembly and connect to the ultrasound transducer 120 to provide power.

Figure 8:
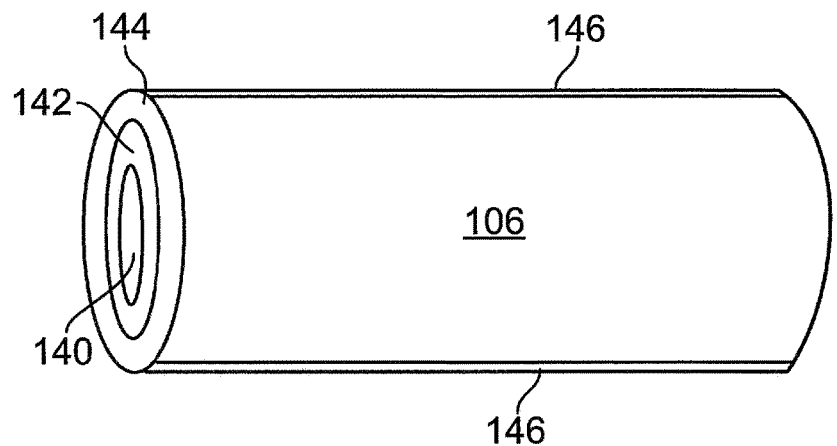
FIG. 8 is a perspective view of one embodiment of an optical fiber in accordance with the present invention.
Figure 9:
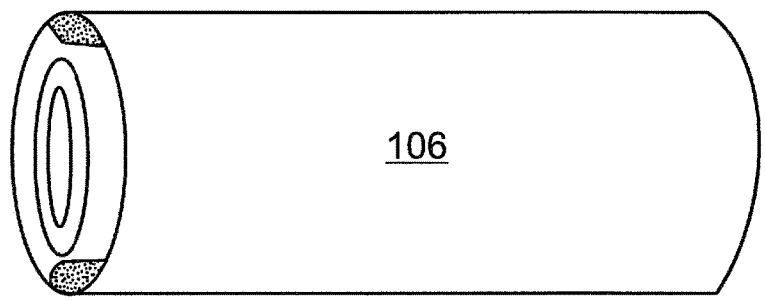
FIG. 9 is a perspective view of another embodiment of an optical fiber in accordance with the present invention.

Turning to FIGS. 8 and 9 the optical fiber 106 described above is formed of a core 140 and two layers, a cladding 142 layer and a buffer 144 layer, surrounding the core 140. At least two electrical conduits or wires 146 are operably associated with wall surfaces of the buffer layer 144, but may, alternatively, be associated with the cladding layer 142 or the core 140.

In the preferred embodiment of the present invention, the optical fiber core 140 is formed of glass made from silica. Nonetheless, other materials known in the art, such as fluorozirconate, fluoroaluminate, and chalcogenide glasses, which are used for longer-wavelength infrared applications, are also within the scope of the present invention. Like other glasses, these glasses have a refractive index of about 1.5. Typically the difference between core and cladding is less than one percent.

As known in the art, the cladding 142 may be formed of a material has a slightly lower refractive index (faster speed) in order to keep the light in the core. The cladding 142 and core 140 make up an optical waveguide.

The cladding 142 is usually coated with a tough resin buffer 144 layer, which may be further surrounded by a jacket layer (not shown), usually plastic. As known in the art, the buffer material surrounding the cladding of a fiber may be a soft plastic material that protects the core 140 from damage. These layers add strength to the fiber but do not contribute to its optical wave guide properties. Rigid fiber assemblies sometimes put light-absorbing ("dark") glass between the fibers, to prevent light that leaks out of one fiber from entering another. This reduces cross-talk between the fibers, or reduces flare in fiber bundle imaging applications.

FIG. 8 illustrates one embodiment of the optical fiber 106, wherein the wires 122 (shown in FIGS. 4, 5, and 7 to be interwinding) are embedded or otherwise coupled on top of the buffer 144 layer of the optical fiber 106. The wires may be formed of metal films vacuum deposited onto the optical fiber or otherwise operably associated with the optical fiber. In another embodiment, as illustrated in FIG. 9, the wires 146 are embedded within the buffer 144 layer of the optical fiber 106.

The present invention may be embodied in other specific forms without departing from its spirit or essential characteristics. The described embodiments are to be considered in all respects only as illustrative and not restrictive. Therefore, the scope of the invention is not limited to the specific exemplary embodiment described above. All changes or modifications within the meaning and range of equivalents are intended to be embraced herein.

As used in this application, the articles "a" and "an" refer to one or more than one (i.e., to at least one) of the grammatical objects of the article. By way of example, "an element" means one element or more than one element.

What is claimed:

1. A catheter comprising:
   an elongate catheter assembly defining a lumen and comprising an outer catheter sheath;
   an imaging assembly disposed within the lumen and comprising an optical coherence tomography (OCT) assembly and an ultrasound transducer, wherein the OCT assembly comprises a ferrule, and wherein the ultrasound transducer is embedded within a wall of the ferrule of the OCT assembly;
   an optical fiber connected to the OCT assembly and comprising a core and a surrounding layer; and
   an electrical wire connected to the ultrasound transducer, wherein the electrical wire is coupled to the core or the surrounding layer of the optical fiber such that the electrical wire and the optical fiber function together as mechanical elements for rotating the imaging assembly;
   wherein the catheter assembly comprises a protection bearing that houses the OCT assembly, the ultrasound transducer, a portion of the optical fiber, and a portion of the electrical wire within the lumen of the catheter assembly and is configured to shield the OCT assembly and the ultrasound transducer, wherein the protection bearing is a tubular housing;
   wherein the OCT assembly and the ultrasound transducer are arranged to obtain imaging data in the same direction through a side of the outer catheter sheath while the imaging assembly rotates such that the OCT assembly and the ultrasound transducer are configured to scan the same or at least partially overlapping spatial areas.

2. The catheter of claim 1, wherein the OCT assembly comprises a gradient index (GRIN) lens assembly and a prism.

3. The catheter of claim 1, wherein at least a portion of the catheter assembly is comprised of a transparent material.

4. The catheter of claim 1, wherein the catheter assembly comprises a material selected from the group consisting of perfluoroalkoxy, polytetrafluoroethylene, fluorinated ethylene propylene, and polyether block amide.

5. The catheter of claim 1, wherein the protection bearing comprises a transparent portion located on a side wall or an end wall of the protection bearing.

6. The catheter of claim 1, wherein the ferrule of the OCT assembly comprises a hollow core, and wherein the optical fiber extends through the hollow core.

7. The catheter of claim 1, wherein the surrounding layer of the optical fiber comprises a cladding layer and a buffer layer, and wherein the electrical wire is coupled to the buffer layer.

8. The catheter of claim 1, wherein the surrounding layer of the optical fiber comprises a cladding layer and a buffer layer, and wherein the electrical wire is embedded within the buffer layer of the optical fiber.

9. A catheter comprising:
   an elongate catheter assembly defining a lumen and comprising an outer catheter sheath;
   an imaging assembly disposed within the lumen and comprising an optical coherence tomography (OCT) assembly and an ultrasound transducer, wherein the OCT assembly comprises a ferrule comprising a cylindrical body, and wherein the ultrasound transducer comprises an angular portion of the cylindrical body;
   an optical fiber connected to the OCT assembly and comprising a core and a surrounding layer; and
   an electrical wire connected to the ultrasound transducer, wherein the electrical wire is coupled to the core or the surrounding layer of the optical fiber such that the electrical wire and the optical fiber function together as mechanical elements for rotating the imaging assembly;
   wherein the catheter assembly comprises a protection bearing that houses the OCT assembly, the ultrasound transducer, a portion of the optical fiber, and a portion of the electrical wire within the lumen of the catheter assembly and is configured to shield the OCT assembly and the ultrasound transducer, wherein the protection bearing is a tubular housing;

wherein the OCT assembly and the ultrasound transducer are arranged to obtain imaging data in the same direction through a side of the outer catheter sheath while the imaging assembly rotates such that the OCT assembly and the ultrasound transducer are configured to scan the same or at least partially overlapping spatial areas.

10. The catheter of claim 9, wherein the OCT assembly comprises a gradient index (GRIN) lens assembly and a prism.

11. The catheter of claim 9, wherein at least a portion of the catheter assembly is comprised of a transparent material.

12. The catheter of claim 9, wherein the catheter assembly comprises a material selected from the group consisting of perfluoroalkoxy, polytetrafluoroethylene, fluorinated ethylene propylene, and polyether block amide.

13. The catheter of claim 9, wherein the protection bearing comprises a transparent portion located on a side wall or an end wall of the protection bearing.

14. The catheter of claim 9, wherein the ferrule of the OCT assembly comprises a hollow core, and wherein the optical fiber extends through the hollow core.

15. The catheter of claim 9, wherein the surrounding layer of the optical fiber comprises a cladding layer and a buffer layer, and wherein the electrical wire is coupled to the buffer layer.

16. The catheter of claim 9, wherein the surrounding layer of the optical fiber comprises a cladding layer and a buffer layer, and wherein the electrical wire is embedded within the buffer layer of the optical fiber.

* * * * *